(12) United States Patent
Deisseroth

(10) Patent No.: US 10,166,284 B1
(45) Date of Patent: Jan. 1, 2019

(54) VACCINES FOR HERPES SIMPLEX VIRUS 1 AND 2

(71) Applicant: MicroVAX, LLC, Warrenton, VA (US)

(72) Inventor: Albert B. Deisseroth, Potomac, MD (US)

(73) Assignee: MicroVAX, LLC, Warrenton, VA (US)

( * ) Notice: Subject to any disclaimer, the term of this patent is extended or adjusted under 35 U.S.C. 154(b) by 0 days.

(21) Appl. No.: 15/689,386

(22) Filed: Aug. 29, 2017

Related U.S. Application Data

(60) Provisional application No. 62/380,516, filed on Aug. 29, 2016.

(51) Int. Cl.
| | |
|---|---|
| C12N 7/00 | (2006.01) |
| A61K 38/17 | (2006.01) |
| A61K 39/12 | (2006.01) |
| A61K 39/42 | (2006.01) |
| C07K 16/28 | (2006.01) |
| C12N 15/86 | (2006.01) |
| C07K 14/005 | (2006.01) |
| A61K 39/00 | (2006.01) |
| A61K 39/245 | (2006.01) |

(52) U.S. Cl.
CPC .... *A61K 39/245* (2013.01); *A61K 2039/5256* (2013.01); *A61K 2039/57* (2013.01); *C12N 2710/10343* (2013.01); *C12N 2710/16634* (2013.01)

(58) Field of Classification Search
CPC ................. A61K 38/177; A61K 39/12; A61K 2039/5256; A61K 39/42; A61K 39/245; A61K 2039/57; C07K 2317/31; C07K 2317/34; C07K 14/005; C07K 16/2878; C12N 7/00; C12N 15/86; C12N 2710/16011; C12N 2710/16611; C12N 2710/16634; C12N 2710/10343
See application file for complete search history.

(56) References Cited

U.S. PATENT DOCUMENTS

| 2002/0147167 | A1* | 10/2002 | Armstrong | ........... | C07K 14/005 514/44 R |
| 2005/0226888 | A1* | 10/2005 | Deisseroth | ......... | A61K 39/0011 424/185.1 |

OTHER PUBLICATIONS

Deisseroth A, Tang Y, Zhang L, Akbulut H, Habib N. TAA/ecdCD40L adenoviral prime-protein boost vaccine for cancer and infectious diseases. Cancer Gene Ther. Feb. 2013;20(2):65-9. doi: 10.1038/cgt.2012.87. Epub Dec. 14, 2012.*
Th Han et al., Vector prime protein boost vaccination in the setting of myeloablative-induced lymphopenia suppresses growth of leukemia and solid tumors, Bone Marrow Transplantation, vol. No. 45, p. 550-557, 2009.
A. Deisseroth et al., TAA/ecdCD40L adenoviral prime-protein boost vaccine for cancer and infectious diseases, Cancer Gene Therapy, vol. No. 20, p. 65-69, 2013.
Hakan Akbulut et al., Chemotherapy Targeted to Cancer Tissue Potentiates Antigen-specific Immune Response Induced by Vaccine for in Vivo Antigen Loading and Activation of Dendritic Cells, Molecular Therapy, vol. 16 No. 10, p. 1753-1760, Oct. 2008.
Pilar Perez-Romero et al., Herpes Simplex Virus Entry Mediator Associates in Infected Cells in a Complex with Viral Proteins gD and at Least gH, Journal of Virology, vol. 79, No. 7, p. 4540-4544, Apr. 2005.
Florent C. Bender, et al., Antigenic and Mutational Analyses of Herpes Simplex Virus Glycoprotein B Reveal Four Functional Regions, Journal of Virology, vol. 81, No. 8, p. 3827-3841, Apr. 2007.
Ekaterina E. Heldwein et al., Crystal Structure of Glycoprotein B from Herpes Simplex Virus 1, Science, vol. No. 313, p. 217-220, Jul. 14, 2006.
Francesca Cocchi et al., The soluble ectodomain of herpes simplex virus gD contains a membrane-proximal pro-fusion domain and suffices to mediate virus entry, PNAS, vol. 101, No. 19, p. 7445-7450, May 11, 2004.
Paolo Di Giovine et al., Structure of Herpes Simplex Virus Glycoprotein D. Bound to the Human Receptor Nectin-1, PLoS Pathogens, vol. 7, No. 9, p. 1-13, Sep. 2011.
Guoying Zhou et al., Engineered herpes simplex virus 1 is dependent on IL13Rα2 receptor for cell entry and independent of glycoprotein D receptor interaction, PNAS, vol. 99. No. 23, p. 15124-15129, Nov. 12, 2002.
Sona Chowdhury et al., Amino acid differences in glycoproteins B (gB), C (gC), H (gH) and L(gL) are associated with enhanced herpes simplex virus type-1 (McKrae) entry via the paired immunoglobulin-like type-2 receptor α, Virology Journal, vol. 9, p. 112-119, 2012.
Yucheng Tang et al., Multistep process through which adenoviral vector vaccine overcomes anergy to tumor-associated antigens, Blood, vol. 104, p. 2704-2713, 2004.
Yu Cheng Tang et al., Use of CD40L, immunoconjugates to overcome the defective immune response to vaccines for infections and cancer in the aged, Cancer Immunol Immunother, vol. 58, p. 1949-1957, 2009.
Yucheng Tang et al., Vector Prime/Protein Boost Vaccine That Overcomes Defects Acquired during Aging and Cancer, The Journal of Immunology, vol. 177, p. 5697-5707, 2006.
Hakan Akbulut et al., Antitumor immune response induced by i.t. injection of vector-activiated dendritic cells and chemotherapy suppresses metastatic breast cancer, Mol Cancer Ther, vol. 5, p. 1975-1985, 2006.

*Primary Examiner* — Rachel B Gill
(74) *Attorney, Agent, or Firm* — Jacob Frank; Glenn Snyder

(57) ABSTRACT

The present invention is directed to novel compositions and methods against HSV (herpes simplex virus) 1 and 2. In brief, an epitope from a binding region of glycoprotein gD, important for binding or attachment of the HSV to the host cell, which is used to mediate the first essential function of infection, and three epitopes from binding regions of glycoprotein gB are used to mediate the second essential function of infection or the fusion of the HSV envelope with the cellular plasma membrane. Each of these epitopes is fused or linked with the extracellular domain of protein CD40L, to form a fusion protein, which fusion proteins are then combined in a mixture to form the inventive composition for acting against HSV 1 and 2.

5 Claims, No Drawings

Specification includes a Sequence Listing.

(56) References Cited

OTHER PUBLICATIONS

Lixin Zhang, et al., An adenoviral vector cancer vaccine that delivers a tumor-associated antigen/CD40-ligand fusion protein to dendritic cells, PNAS, vol. 100, No. 25, p. 15101-15106, Dec. 9, 2003.

Yucheng Tang et al., Vaccine strategies for cancer and infectious diseases in the elderly, Gene Therapy, p. 2-11, 2007.

* cited by examiner

```
SEQUENCE LISTING

<160> NUMBER OF SEQ ID NOS: 4

<210> SEQ ID NO 1
<211> LENGTH: 49
<212> TYPE: PRT
<213> ORGANISM: Artificial Sequence
<220> FEATURE:
<223> OTHER INFORMATION: Synthetic Construct

<400> SEQUENCE: 1

Pro Asn Ala Thr Gln Pro Glu Leu Ala Pro Glu Asp Pro Glu Asp Ser
1               5                   10                  15

Ala Leu Leu Glu Asp Pro Val Gly Thr Val Ala Pro Gln Ile Pro Pro
            20                  25                  30

Asn Trp His Ile Pro Ser Ile Gln Asp Ala Ala Thr Pro Tyr His Pro
        35                  40                  45

Pro

<210> SEQ ID NO 2
<211> LENGTH: 30
<212> TYPE: PRT
<213> ORGANISM: Artificial Sequence
<220> FEATURE:
<223> OTHER INFORMATION: Synthetic Construct

<400> SEQUENCE: 2

Ser Gly Leu Leu Asp Tyr Thr Thr Glu Val Gln Arg Arg Asn Gln Leu
1               5                   10                  15

His Asp Leu Arg Phe Ala Asp Ile Asp Thr Val Ile His Ala
            20                  25                  30

<210> SEQ ID NO 3
<211> LENGTH: 19
<212> TYPE: PRT
<213> ORGANISM: Artificial Sequence
<220> FEATURE:
<223> OTHER INFORMATION: Synthetic Construct

<400> SEQUENCE: 3

Ser Thr Thr Phe Thr Thr Asn Leu Thr Glu Tyr Pro Leu Ser Arg Val
1               5                   10                  15
```

-continued

```
Asp Leu Asp

<210> SEQ ID NO 4
<211> LENGTH: 22
<212> TYPE: PRT
<213> ORGANISM: Artificial Sequence
<220> FEATURE:
<223> OTHER INFORMATION: Synthetic Construct

<400> SEQUENCE: 4

Pro Leu Leu Ser Asn Thr Leu Ala Glu Leu Tyr Val Arg Glu His Leu
1               5                   10                  15

Arg Glu Gln Ser Arg Lys
            20
```

VACCINES FOR HERPES SIMPLEX VIRUS 1 AND 2

CROSS-REFERENCE TO RELATE APPLICATION

This application claims priority and benefit under 35 USC § 119(e) of U.S. Provisional Patent Application No. 62/380,516, filed on Aug. 29, 2016, the disclosure of which is hereby incorporated by reference herein in its entirety.

FIELD OF THE INVENTION

The present invention relates generally to the field of HSV (herpes simplex virus) infections. More particularly, the invention is directed to novel composition and methods against herpes simplex viral particles.

BACKGROUND OF THE INVENTION

One sixth of the people in the USA are carriers of Herpes Simplex Virus (HSV). The incidence of HSV infections is increasing worldwide. There are 2 strains of HSV: 1 and 2 (1).

HSV-2 is leading cause of genital ulcers worldwide. Five hundred thirty-five (535) million persons in the world are infected with HSV-2 which has an incidence of 24 million infections per year (1).

HSV-1 is the cause of Herpes Labialis (cold sores on the lips). More than one half of the world's population is positive for antibodies against HSV-1. HSV-1 is now becoming a cause of genital ulcers as well (1).

Initial Infection Leads to a Carrier State Which is Life-Long: The initial infection of keratinocytes is followed by infection of sensory nerves. The HSV viral particles are translocated centrally to the Sensory Ganglia in which the HSV resides in a quiescent state until sporadic reactivation of replication by an unknown process. Since the HSV is not localized in the intravascular space, but localizes in sensory ganglia in the extravascular space, which is a sanctuary that is not easily penetrated by neutralizing antibodies, the HSV infection is never completely cleared by the immune response.

Vaccines/Compositions for HSV

Many vaccines have trials which fail and many more fail in development. DNA vaccines with lipid adjuvant are popular (1). Vaccination with gB, gC, gD, gH and gL induce neutralizing antibodies in the blood stream. But these neutralizing antibodies do not protect animals completely since the HSV is protected from the neutralizing antibodies by its location in the sensory ganglia sanctuary site. Sporadically, the intracellular replication of HSV is triggered by unknown factors and the viral particles produced are translocated within sensory nerves to keratinocytes where the formation of ulcers result (8).

Chiron studied a recombinant gD2 vaccine which induced neutralizing antibodies (8). The administration of this vaccine reduced the rate of monthly occurrences of sores from 0.18 to 0.9/month in one of three trials but failed to reduce rates in two other trials (8). The third trial was in young seronegative women (8). Such difficulty with the development of an effective vaccine for HSV is thought to be due to the requirement to induce very high levels of neutralizing antibodies to penetrate nerves (sensory ganglia) to prevent transfer from sensory nerves to keratinocytes. It is harder to protect or to suppress outbreaks of HSV since the virus is not hematogenously disseminated.

The World Health Organization (WHO) has indicated that antiviral medications, such as acyclovir, famciclovir, and valacyclovir, are the most effective medications available for people infected with HSV. These can help you, according to the WHO, to reduce the severity and frequency of symptoms, but cannot cure the infection. (20)

In a recent publication by the University of Pennsylvania on research done by a team led by Dr. Harvey M. Friedman, it states that studies establish an important role for gC and gE-mediated immune evasion in HSV-1 pathogenesis. Also, it states that gC demonstrates an important therapeutic role in immune evasion. Further, this group has found that a gC/gD2/gE2 trivalent subunit antigen vaccine is highly effective as therapy for prior genital herpes. (21)

Applicant's TAA/ecdCD40L Vaccine/Composition Platform

The TAA/ecdCD40L vaccine/composition platform is based on the attachment of a fragment of a target associated antigen (TAA) to the extracellular domain (ecd) of the potent immunostimulatory signal CD40 ligand (CD40L). The antigen specific vaccine can be administered either as a TAA/ecdCD40L protein, or as an expression vector encoding the TAA/ecdCD40L such as the adenoviral vector (Ad-sig-TAA/ecdCD40L), or a plasmid DNA expression vector. The vaccine can also be administered as a vector prime followed in 7 and 21 days with subcutaneous (sc) injections of the TAA/ecdCD40L protein vaccine/composition. This vaccine/composition platform was developed by Applicant's laboratory (9-19) to overcome the following problems: weak immunogenicity of the target antigens, qualitative or quantitative defects of CD4 helper T cells, defective response in immunodeficient individuals including the older aged population due to diminished expression of CD40L in activated CD4 helper T cells, and/or low levels of presentation of target antigens on Class I or II MHC on dendritic cells (DCs). The CD40L is important for the expansion of antigen specific CD8 effector T cells and antigen specific B cells in response to vaccination.

Activation of DCs by TAA/ecdCD40L Vaccine. The activated TAA loaded DCs then migrate to the regional lymph nodes (9, 13) where they can activate and induce expansion of the TAA specific $CD8^+$ effector T cells. These antigen specific $CD8^+$ effector cells become increased in number in the lymph nodes (9, 13), and they then egress from the lymph nodes into the peripheral blood. The antigen specific CD8 effector T cells exit the intravascular compartment and enter into the extra-vascular sites of inflammation or infection (16-17 and 19). In addition to showing that this vaccine increases the levels of the antigen specific $CD8^+$ effector T cells in the sites of inflammation or infection (19), the Applicant's laboratory has shown that the activation and expansion of the B cells by the TAA/ecdCD40L protein increases the levels of the TAA specific antibodies including neutralizing antibodies against viral antigens in the serum (16-17 and 19).

Impact of Attachment of TAA to CD40L. The attachment of fragments of the TAA to the CD40L accomplishes two objectives:
 1. The binding of the TAA/ecdCD40L protein to the CD40 receptor on the DCs as well as on the B cells and T cells, activating these cells thereby promoting a potent immune response (9, 11 and 13); and 2. Once the TAA/ecdCD40L protein is engaged on the CD40 receptor of the DC, the entire TAA/ecdCD40L protein is internalized into the DC in a way that allows Class I as well as Class II MHC presentation of the TAA (9, 13).

Modes of Administration. There are four versions of this vaccine/composition: 1. One in which the TAA/ecdCD40L transcription unit is embedded in a replication incompetent adenoviral vector (Ad-sig-TAA/ecdCD40L); 2. One in which the vector is used as an initial priming injection, followed by two sc injections of the TAA/ecdCD40L protein; 3. One in which the vaccine/composition consists solely of the TAA/ecdCD40L protein; and 4. One in which the TAA/ecdCD40L is inserted into a plasmid DNA expression vector. The TAA is connected through a linker to the aminoterminal end of the ecd of the potent immunostimulatory signal CD40L.

Definitions

As used herein, the term "antigen" refers broadly to any antigen or portion thereof to which a human, mammal, bird or other animal can generate an immune response. "Antigen" as used herein refers broadly to a molecule that contains at least one antigenic determinant to which the immune response may be directed. The immune response may be cell-mediated, humoral or both.

"Pharmaceutically acceptable" in the context of the present invention means a pharmaceutical composition that is generally safe, non-toxic and biologically acceptable for veterinary and human pharmaceutical use. Preferred compositions of this invention are intended for humans or animals.

The phrase "an effective amount" in reference to administering the fusion protein or an expression vector encoding that protein, is an amount that results in an increase in the immune response as measured by an increase in T cell activity and/or antibody production.

The fusion protein recited herein may be formulated with an adjuvant to enhance the resulting immune response. As used herein, the term "adjuvant" in the context of the instant invention means a chemical that, when administered with the expression vector or the fusion protein, enhances the immune response. An adjuvant is distinguished from a carrier protein in that the adjuvant is not chemically coupled to the antigen. Adjuvants are well known in the art and include, but not limited to, mineral oil emulsions (U.S. Pat. No. 4,608,251) such as Freund's complete or Freund's incomplete adjuvant (Freund, *Adv. Tuberc. Res.* 7:130 (1956); Calbiochem, San Diego Calif.), aluminum salts, especially aluminum hydroxide or ALHYDROGEL (approved for use in humans by the U.S. Food and Drug Administration), muramyl dipeptide (MDP) and its analogs such as [Thr$^1$]-MDP (Byersand Allison, *Vaccine* 5:223 (1987)), monophosphoryl lipid A (Johnson et al., *Rev. Infect. Dis.* 9:S512 (198)), and the like.

The term "vector" which contains a transcription unit (aka the "expression vector") as used herein refers to viral and non-viral expression vectors that when administered in vivo can enter target cells and express an encoded protein. Viral vectors suitable for delivery in vivo and expression of an exogenous protein are well known and include adenoviral vectors, adeno-associated viral vectors, retroviral vectors, vaccinia vectors, pox vectors, herpes simplex viral vectors, and the like. Viral vectors are preferably made replication defective in normal cells. For example, see U.S. Pat. Nos. 6,669,942; 6,566,128; 6,794,188; 6,110,744; 6,133,029. The vector can be administered parenterally, such as intravascularly, intravenously, intra-arterially, intramuscularly, subcutaneously, or the like. Administration can also be orally, nasally, rectally, transdermally or aerosol inhalation. The vectors may be administered as a bolus, or slowly infused. The vector in the instant application is preferably administered subcutaneously.

The term "transcription unit" as it is used herein in connection with an expression vector means a stretch of DNA that is transcribed as a single, continuous mRNA strand by RNA polymerase, and includes the signals for initiation and termination of transcription. The transcription unit is in operable linkage with transcriptional and/or translational expression control elements such as a promoter and optionally any upstream or downstream enhancer element(s). A useful promoter/enhancer is the cytomegalovirus (CMV) immediate-early promoter/enhancer. See U.S. Pat. Nos. 5,849,522 and 6,218,140.

The term "CD40 ligand" (CD40L) as used herein refers to a full length or portion of the molecule known also as CD154 or TNF5. CD40L is a type II membrane polypeptide having a cytoplasmic domain at its N-terminus, a transmembrane region and then an extracellular domain (ecd) at its C-terminus. Unless otherwise indicated the full length CD40L is designated herein as "CD40L," "wtCD40L" or "wtTmCD40L." The nucleotide and amino acid sequence of CD40L from mouse and human is well known in the art and can be found, for example, in U.S. Pat. No. 5,962,406. Also, included within the meaning of CD40 ligand are variations in the sequence including, but not limited to, conservative amino acid changes and the like which do not alter the ability of the ligand to elicit an immune response in conjunction with the fusion protein of the invention.

The term "neutralizing antibody" as used herein refers to antibodies that reduce the virulence, infectivity or pathogenicity of HSV by partial or complete inactivation of one or more HSV virulence factors.

The term "secretion" in reference to the fusion protein TAA/ecdCD40L, means that the fusion protein includes elements (such as the secretory or signal sequence) that cause secretion of the TAA/ecdCD40L fusion protein to occur, as opposed to an element such as a transmembrane domain of a cell that does not allow secretion to occur.

Some of the abbreviations used herein include: "Ad" (adenoviral); "sig" (signal sequence); "TAA" (target associated antigen); "ET" (epitope target); "ecd" (extracellular domain); and "sc" (subcutaneous).

DETAILED DESCRIPTION OF THE INVENTION

Structure of HSV and the Process of Infection of Cells by HSV: The HSV-1 and HSV-2 viruses consist of 150 kB of DNA surrounded by a capsid which is enveloped in a lipid bilayer. The lipid bilayer contains 12 glycoproteins. Among these, the following glycoproteins: gB, gD, gH and gL, participate in viral cell entry and are required for fusion of the viral lipid bilayer envelope with the plasma membrane of the target cell, which is required for infection (2). The first step is the binding of gD to one of the 3 following receptors: nectin-1, herpesvirus entry mediator (HVEM) and a specifically modified heparan sulfate (3-O-sulfated proteoglycans) (2). Binding of gD to HVEM induces a conformal change in gD which itself induces a displacement of the C terminus of the ecd of gD resulting in the exposure of the N terminus of gD to the receptor. These changes in gD then lead to interactions with gB which along with gH and gL induce fusion of the viral envelope with the plasma membrane of the cell (2). In summary, gD mediates the first essential function of infection: the initial binding of HSV to cellular receptors, and gB mediates the second essential function of infection: fusion of the HSV envelope with the cellular plasma membrane.

Applicant has taken a different path than to seek an effective therapeutic composition for HSV 1 & HSV 2, than that taken by many others in the prior art, including those approaches addressed above. Glycoprotein gD: As outlined above, the attachment of the virus to the target cell, is mediated through an essential interaction of gD with one of the three following cellular receptors: nectin-1, herpes virus entry mediator, and a specifically modified heparin sulfate (3-5). The receptor binding regions of gD reside between AA residues 1-243 (4).

The binding of gD with any of these 3 cellular receptors results in conformational changes in gD in which the C-terminal fragment opens and becomes available for interaction with gB to trigger molecular rearrangements with gB, gH and gL which are necessary for fusion of the outer membrane of herpes with the cell membrane (2). A series of binding and infectivity assays designed to measure truncation and fusion were used to study the effects of mutational change in gD. These studies showed that the membrane proximal region of full-length gD (residues 261-305) are critical for HSV infectivity and cell-cell fusion (4). A soluble gD region containing the whole ectodomain of gD allows entry of a gD null virus in receptor expressing cells whereas a truncated form of gD lacking residues 260-316 does not allow entry (4).

The amino acid sequence of this critical binding region of gD is as follows (4):
AA261-PNATQPELAPEDPEDSALLEDPVGTVAPQIPP-NWHIPSIQDAATPYHPP-AA308 SEQ ID No. 1
Following attachment of the HSV to the plasma membrane receptors of the mammalian cell, gD recruits gB so that it induces fusion of the HSV envelope with the plasma membrane of the cell (6). This fragment of HSV gD contains epitopes which bind to MHC Class I as well as MHC Class II.

Glycoprotein gB: There are 3 highly conserved regions in gB to which neutralizing antibodies have been isolated:
a. The region at the junction of Domain I with Domain V is recognized by neutralizing antibody SS106 (2). This region consists of residues present in helix alpha F of domain V and residues present in the neighboring domain I (2). The amino acid sequence of this fragment (AA697-AA725 of gB) is as follows (2):
AA697-SGLLDYTTEVQRRNQLHDLRFADIDTVIHA-AA725 SEQ ID No. 2
b. In Domain II of the HSV gB protein, is a region recognized by neutralizing antibody H1839 (2) which is in AA 391-AA410. The location of these epitopes which are recognized by neutralizing antibody H1839 demonstrate the critical role of this fragment of gB for the infectivity of HSV (2). The amino acid sequence of this fragment (AA391-AA 410) of gB is as follows (7):
AA391-STTFTTNLTEYPLSRVDLD-AA410 SEQ ID No. 3
c. In Domain II of the HSV gB protein, is a region recognized by neutralizing antibody H1784 (2) which is in AA 454-AA 475. The location of these epitopes which is recognized by neutralizing antibody H1784 demonstrates the critical role of this fragment of gB for the infectivity of HSV (2). The amino acid sequence of this fragment (AA454-AA 475) of gB is as follows (7):
AA454-PLLSNTLAELYVREHLREQSRK-AA475 SEQ ID No. 4
Each of these fragments of HSV gB (SEQ. ID NOS. 2, 3, and 4) contains epitopes which bind to MHC Class I as well as MHC Class II.

Rationale and Objectives of the Applicant's Invention of a vaccine for HSV. The objective of attaching antigenic fragments from the HSV gB and HSV gD proteins (see SEQ ID No. 1-4) to the ecdCD40L is to induce levels of neutralizing antibody that are sufficiently high so as to totally block the infectivity of HSV viral particles that are released from sensory neurons so as to prevent infection of keratinocytes that would lead to ulcerations (sores on the lips and genital mucosal surfaces): i.e. to maintenance of latency of clinical manifestations of the HSV infection.

Previous pre-clinical studies in the mouse have shown that the attachment of antigenic fragments of the hemagglutinin antigen of influenza A to the CD40L result in very high titers of neutralizing antibodies to influenza A (16) and that there is induction of a memory response for up to a year (9).

Neutralizing antibodies to gB and gD, would block transfer of HSV from sensory nerves to keratinocytes. But the level of these neutralizing antibodies must be high to penetrate sufficiently the tissues to block transfer of HSV from sensory nerves to keratinocytes. The invention proposed by Applicant includes the linking of one fragment of HSV gD that is necessary for binding of the virus to cellular receptors (SEQ ID No. 1), and 3 fragments of gB that are necessary for inducing fusion of the HSV viral envelope to the plasma membrane of target cells. The unique invention by Applicant is to use the TAA/ecdCD40L to induce high enough levels of neutralizing antibodies such that the sensory ganglia are penetrated sufficiently so that the spontaneous reactivation of HSV infectious life cycle of the virus is permanently suppressed.

This is the first vaccine/composition and technology which utilizes a property of the TAA/ecdCD40L technology to suppress HSV particles being released from sensory nerves thereby preventing infection of keratinocytes. All other neutralizing antibodies induced by vaccines are binding to viruses in the intravascular space in the blood stream. This invention is designed to induce binding of neutralizing antibodies to viral particles in sensory ganglia or at the neural synapse of sensory nerves with keratinocytes.

Method of Selection of Antigenic Fragments from HSV gB and HSV gD Proteins for Attachment to ecdCD40L.
The criteria for selection of antigenic fragments for attachment to the ecdCD40L are as follows:
 a. select a fragment that is needed for the functions of viral attachment to cellular plasma membrane and induction of fusion of HSV lipid envelop and cellular plasma membrane so that the binding of neutralizing antibodies to HSV will render the HSV non-infective;
 b. select the fragment size so that it will not disrupt the trimeric structure of the ecdCD40L protein when the HSV TAA fragment is attached to the ecdCD40L;
 c. the antigenic fragment is composed of a continuous stretch of amino acids and is not denaturable;
 d. The fragment must contain amino acid fragments that bind to Class I as well as Class II MHC. We are hypothesizing that the attachment of peptide fragments from gD and gB proteins of HSV (which contain both fragments that bind both Class I and Class II MHC) will lead to induction of high titers of neutralizing antibodies to these fragments of HSV gD and gB, but also to increased levels of CD8 effector T cells which are specific for the fragments of HSV proteins gD and gB. The induction of increased levels of CD8 effector T cells to the fragments of HSV gD and HSV gB proteins may lead to clearance of HSV infected cells (sensory ganglia and keratinocytes), whereas historically, the induction of neutralizing antibodies to gD and gB HSV proteins in the past (through vaccination) have failed to clear the HSV infection, presumably due to poor penetration of the neutralizing antibodies into the sanctuary sites which are responsible for the continuation of the HSV infection on a lifelong basis.

Four fragments were chosen: one from HSV gD and three fragments from HSV gB. The one fragment chosen from gD (SEQ ID No. 1) was shown to be absolutely essential for the binding of HSV to the receptors for gD (3-5). In addition, this fragment was shown to be the target for neutralizing antibodies.

The 3 fragments chosen from HSV gB were chosen because they had been shown to be important in the gB mediated fusion of the viral envelope with the cellular plasma membrane. Also, they were targeted by neutralizing antibodies for HSV (2).

All four of these fragments contained epitopes defined by continuous stretches of amino acids and were not subject to denaturation. These "continuous epitopes" would therefore be less likely to be sites of immunological escape. The fact that there are four antigenic targets of the vaccine would also reduce the likelihood of immunological escape.

Description of HSV TAA/ecdCD40L Vaccine: The Applicant's TAA/ecdCD40L vaccine is a mixture of 4 fusion proteins encoded by viral or plasmid expression vectors which contain transcription units encoding the SEQ ID Nos. 1-4 presented above each linked to the ecdCD40L by a 9 AA linker as follows:

1. pHSVgDAA$_{260-308}$/ecdCD40L which encodes SEQ ID No. 1 linked to ecdCD40L
2. pHSVgBAA$_{697-725}$/ecdCD40L which encodes SEQ ID No. 2 linked to ecdCD40L
3. pHSVgBAA$_{391-410}$/ecdCD40L which encodes SEQ ID No. 3 linked to ecdCD40L
4. pHSVgBAA$_{454-475}$/ecdCD40L which encodes SEQ ID No. 4 linked to ecdCD40L This plasmid DNA vaccine/composition is administered intramuscularly (IM) as a mixture of the 4 above described plasmid expression vectors (10 micrograms of DNA for each). These injections are administered at Days 1, 8 and 21 and then monthly for 6 additional vaccinations until they suppress outbreaks of HSV ulcers in individual in whom such ulcers have been occurring on a monthly basis. Although it is Applicant's preference that four separate vaccines/compositions are generated and then mixed together to form a single vaccine/composition as stated, it is believed that the three HSV gB epitopes could alternatively be strung together and linked to ecdCD40L to form a single vaccine/composition that could then be mixed with the vaccine/composition HSV gD epitope which is linked to ecdCD40L.

Aspects of the Invention: The attachment of the fragments of HSV proteins gD and gB have two possible effects on protecting uninfected individuals or in clearing pre-existing infections:

1. The attachment of the fragments of HSV gD and HSV gB proteins to the ecd of CD40L increase the titers of neutralizing antibodies to antigenic fragments in gD (SEQ ID No. 1) and antigenic fragments in gB (SEQ ID Nos. 2-4) so that the neutralizing antibodies generated by the vaccine have increased capability to penetrate into the extravascular sites which HSV infectious particles exist (sensory ganglia);

2. The attachment of the fragments of HSV gD and HSV gB proteins to the ecd of CD40L increase the levels of CD8 effector T cells which are specific for the HSV antigenic fragments of gD and gB. This could possibly make the HSV/ecdCD40L vaccine/composition described herein successful in fully protecting individuals against HSV or making it possible for the HSV/ecdCD40L vaccine/composition to clear a pre-existing infection through CD8 effector T cell killing of HSV infected cells. Any infectious HSV particles released by the cells killed by the CD8 effector T cells would be rendered non-infectious by the neutralizing antibodies induced by the vaccination.

REFERENCES

1. Perez-Romero P, Perez kA, Capul A, Montgomery R and Oveta Fuller A. Herpes Simplex virus entry mediator associates in infected cells in a complex with viral proteins gD and at least gH. Journal of Virology 79: 4540-4544, (2005).
2. Bender F C, Samanta M, Heldwein E E, Ponce de Leon M, Bilman E, Lou H, Whitbeck J C, Eisenberg R J, and Cohen G H. Antigenic and Mutational analyses of Herpes Simplex virus glycoprotein B reveal four functional regions. Journal of Virology 81: 3827-3841, (2007).
3. Heldwein E E, Lou H, Bender F C, Cohen G H, Eisenberg R J, and Harrison S C. Crystal structure of Glycoprotein B from Herpes Simplex virus 1. Science 313: 217-220, (2006).
4. Cocchi F, Fusco D, Menotti L, Gianni T, Eisenberg R J, Cohen G H, and Campadelli-Fiume G. The soluble ectodomain of herpes simplex virus gD contains a membrane-proximal pro-fusion domain and suffices to mediate virus entry. PNAS 101: 7445-745, (2004).
5. Di Giovine P, Settembre E C, Bhargava A K, Luftig M A, Lou H, Cohen G H, Eisenberg R J, Krummenacher C, and Carfi A. Structure of Herpes Simplex virus glycoprotein D bound to the human receptor Nectin-1. PLoS Pathogens 7: e1002277 (pages 1-13), 2011.
6. Zhou G Y, Ye G J, Debinski W, and Roizman B. Engineered herpes simplex virus 1 is dependent on IL13Ralpha2 receptor for cell entry and independent of glycoprotein D receptor interaction. PNAS 99: 15124-15129, (2002).
7. Chowdhury S, Naderi M, Chouljenko V N, Walker J D, and Kousoulas K G. Amino acid differences in glycoproteins B(gB), C (gC). J )gH), and L(gL) are associated with enhanced herpes simplex virus type-1 entry via the paired immunoglobulin-like type-2 receptor alpha. Virology Journal 9: 112-119, (2012).
8. Stanberry L R, and Belshe R. Herpes Simplex virus vaccines. Chapter 50 (pp. 1090-1096) in Vaccines (6th Edition), Editors: Plotkin S A, Orenstein W A, and Offit P A. Elsevier/Saunders, 2013.
9. Zhang, L, Tang, Y, Akbulut H, Zelterman D, Linton P-J, and Deisseroth, A. An adenoviral vector cancer vaccine that delivers a tumor-associated antigen/CD40-ligand fusion protein to dendritic cells. PNAS, 100: 15101-15106, (2003).
10. Akbulut, H, Tang, Y, Maynard J, Zhang L, Pizzorno G, and Deisseroth, A. Vector targeting makes 5-fluorouracil chemotherapy less toxic and more effective in animal models of epithelial neoplasms. Clin Cancer Res 10: 7738-7746, (2004).
11. Tang, Y, Zhang, L, Yuan, J, Akbulut H, Maynard J, Linton P-J, and Deisseroth, A. Multistep process through which adenoviral vector vaccine overcomes anergy to tumor-associated antigens. Blood, 104: 2704-2713, (2004).
12. Akbulut H, Tang Y C, Akbulut K G, Maynard J, Zhang L, Deisseroth A. Antitumor immune response induced by i.t. injection of vector activated dendritic cells and chemotherapy suppresses metastatic breast cancer. Mol Cancer Ther 5:1975-1985, (2006).
13. Tang Y C, Maynard J, Akbulut H, Fang X M, Zhang W W, Xia X Q, Koziol J, Linton P-J, and Deisseroth A. Vaccine which overcomes defects acquired during aging and cancer. Journal of Immunology 177:5697-5707, (2006).
14. Tang Y, Akbulut H, Maynard J, Zhang L, Petersen L, and Deisseroth A. Vaccine strategies for cancer and infectious diseases in the elderly. Gene Therapy, Eds. Takenori Ochiai, Hideaki Shimada, and Masatoshi Tagawa, Published by Japanese Ministry of Education and Science, pp. 78-85, (2007).
15. Akbulut H, Akbulut K G, Tang Y C, Maynard J and Deisseroth A. Chemotherapy targeted to cancer tissue potentiates antigen specific immune response induced by vaccine for In vivo antigen loading and activation of dendritic cells. Molecular Therapy, 10:1753-1760, (2008).
16. Tang, Y C, Linton, P J, Thoman, M, and Deisseroth A. Symposium in Writing: Vaccine for infections and cancer. Cancer Immunology and Immunotherapy, 58: 1949-1957, (2009).
17. Han T H, Tang, Y C, Park Y H, Petersen L, Maynard J, Li P C, and Deisseroth A. Ad-sig-BcrAbl/ecdCD40L vector prime-BcrAbl/ecdCD40L protein boost vaccine for P210Bcr-Abl protein. Bone Marrow Transplantation, (2009).
18. Akbulut H, Tang Y, Akbulut K G, Maynard J, and Deisseroth A. Addition of adenoviral vector targeting of chemotherapy to the MUC-1/ecdCD40L VPPP vector prime protein boost vaccine prolongs survival of mice carrying growing subcutaneous deposits of Lewis lung cancer cells. Gene Therapy, 17: 1333-1340, (2010).
19. Deisseroth A, Tang Y, Zhang L, Akbulut H, and Habib N. TAA/ecdCD40L adenoviral prime-protein boost vaccine for cancer and infectious diseases. Cancer Gene Therapy 20: 65-69, (2013).

The invention claimed is:

1. A pharmaceutical composition for inducing a humoral and cellular immune response against HSV (herpes simplex virus) 1 and HSV 2 in an individual by primarily mediating two essential functions of HSV infection, said composition comprising four expression vectors:
   wherein the first essential function is mediated by a first expression vector which encodes an extracellular domain of the CD40 ligand (ecdCD40L) fused at the amino terminus to an epitope SEQ ID NO: 1 of HSV glycoprotein D (gD); and
   wherein the second essential function is mediated by:
   (a) a second expression vector which encodes an ecdCD40L fused at its amino terminus to a first epitope SEQ ID NO: 2 of HSV glycoprotein B (gB);
   (b) a third expression vector which encodes an ecdCD40L fused at its amino terminus to a second epitope SEQ ID NO: 3 of HSV glycoprotein gB; and,
   (c) a fourth expression vector which encodes an ecdCD40L fused at its amino terminus to a third epitope SEQ ID NO: 4 of HSV glycoprotein gB:
   wherein said gD and gB epitopes are distinct from one another and are recognized by neutralizing antibodies.

2. A pharmaceutical composition according to claim 1, wherein each of said HSV gD and HSV gB epitopes contains amino acids that allow for presentation via both MHC Class I and MHC Class II pathways.

3. A pharmaceutical composition according to claim 1, wherein said expression vectors are adenoviral expression vectors.

4. A pharmaceutical composition according to claim 1, wherein said expression vectors are plasmid expression vectors.

5. A pharmaceutical composition for inducing a humoral and cellular immune response against HSV (herpes simplex virus) 1 and HSV 2 in an individual by primarily mediating two essential functions of HSV infection, said composition comprising two expression vectors:
   wherein the first expression vector encodes an extracellular domain of the CD40 ligand (ecdCD40L) fused at the amino terminus to epitope SEQ ID NO: 1 of HSV glycoprotein D (gD);
   wherein the second expression vector encodes an ecdCD40 ligand fused at its amino terminus to three epitopes linked together including a first epitope SEQ ID NO: 2 of HSV glycoprotein B (gB);
   a second epitope SEQ ID NO: 3 of HSV glycoprotein gB; and,
   a third epitope SEQ ID NO: 4 of HSV gB,
   wherein said gD and gB epitopes are distinct from one another and are recognized by neutralizing antibodies.

* * * * *